United States Patent [19]

Pettiford

[11] Patent Number: 4,934,389
[45] Date of Patent: Jun. 19, 1990

[54] DENTAL FLOSS DISPENSER

[76] Inventor: William L. Pettiford, 1908 Q St., S.E., Washington, D.C. 20020

[21] Appl. No.: 280,450

[22] Filed: Dec. 6, 1988

[51] Int. Cl.⁵ ............................................. A61C 15/00
[52] U.S. Cl. ..................................... 132/325; 132/324
[58] Field of Search ............... 132/321, 322, 323, 324, 132/325, 326, 327, 328, 329, , 309; 206/63.5, 368

[56] References Cited

U.S. PATENT DOCUMENTS

| | | | |
|---|---|---|---|
| 1,050,560 | 1/1913 | Moore | 132/321 |
| 1,439,076 | 12/1922 | Edwards | 132/314 |
| 1,488,810 | 4/1924 | Fraser | 132/321 |
| 2,893,405 | 7/1959 | Castelli | 132/321 |
| 3,853,134 | 12/1974 | McCord | 132/309 |
| 4,141,519 | 2/1979 | Tarrson | 132/321 |
| 4,162,688 | 7/1979 | Tarrson et al. | 132/322 |
| 4,673,106 | 6/1987 | Fishman | 132/309 |
| 4,796,783 | 1/1989 | Paulson | 132/325 |

Primary Examiner—Gene Mancene
Assistant Examiner—Adriene J. Lepiane
Attorney, Agent, or Firm—Rodger H. Flagg

[57] ABSTRACT

A dental floss dispenser is disclosed, which may be adapted for insertion into an existing cavity found in pump type tooth paste dispensers, or the dental floss dispenser may be used separately without modification. The dental floss dispenser has a housing formed of a base, a circumferential wall extending from the base, and a cap secured to the circumferential wall. A chamber is thus formed between the base, the circumferential wall and the cap for rotatably receiving a dental flose spool therein. The cap has an aperture therethrough, and a hinged portion which may be raised or lowered; a knife blade is secured to the hinged portion in spaced relation from the aperture, and the dental floss is drawn through the aperture and closely received between the knife blade and the hinged portion, and biased to cut the end of the dental floss. The hinged portion of the cover is then closed to secure the knife blade and the portion of the dental floss extending between the knife blade and the aperture from external contamination between use.

20 Claims, 2 Drawing Sheets

DENTAL FLOSS DISPENSER

TECHNICAL FIELD

The present invention relates to a dispenser for dental floss adapted for insertion into the base of a toothpaste dispenser, or for alternate use as a separate unit. Dental floss is primarily used by consumers for cleaning teeth by drawing the dental floss between teeth to dislodge food particles after eating.

BACKGROUND OF THE INVENTION

Dental floss dispensers having an outer housing, a cap, a dispensing aperture, and a cut off blade are known to the art.

Toothpaste dispensers, such as the pump type toothpaste dispensers, are also known in the art. These items require separate space in an often crowded medicine cabinet, and are often unhandy to use where these items must compete for space with other toiletry items, such as a toothbrush, comb, razor, shaving cream, fragrances, lotions, oils, tweezers, brush, etc. These items often accompany the user on trips, where they must be repeatedly packed an unpacked. Numerous efforts have been made to combine one or more of these items to reduce the overall clutter while providing the necessary accouterments and toiletry items now in common use by men, women and children.

U.S. Pat. No. 3,853,134 discloses a combination toothbrush and dental floss dispenser, wherein dental floss is stored and dispensed from the handle of a toothbrush.

U.S. Pat. No. 4,673,106 discloses a combination tooth paste and dental floss dispenser, wherein dental floss is stored and dispensed from the base of a tooth paste dispenser.

DISCLOSURE OF THE INVENTION

The dental floss dispenser disclosed herein is ideally suited for use in crowded or cramped quarters which are often found in proximity to a basin where toiletries are often stored, or for use on trips where space and weight are at a premium. The dental floss dispenser of the present invention may be inserted within the base of a tooth paste pump type dispenser, or may be separately used, in accordance with the preference of the user.

An embodiment of the dental floss dispenser of this invention comprises a hinged cap secured to a housing sized to rotatably receive a spool of dental floss therein. The dental floss passes from within the housing through an aperture adjacent to the hinged portion of the hinged cap, and extends to a knife blade which is positioned adjacent to the hinged cap to retain the dental floss between the knife blade and the hinged cap. A recess is disposed in the hinged cap between the aperture and the knife blade to aid in manually grasping the end of the dental floss in preparation for pulling the floss through the aperture from the spool.

Once a suitable length of the dental floss is pulled through the aperture by the user, the dental floss is drawn between the knife blade and the hinged cap, and pulled to bias the dental floss against the knife blade to cut the dental floss to the desired length.

The close proximity of the knife blade to the hinged cap serves to retain the end of the dental floss between the knife blade and the hinged cap between use. The hinged cap may then be closed to protect the exposed portion of the dental floss extending between the knife blade and the aperture from the surrounding environment.

The above mentioned features and objects of this invention and the manner of attaining them will become more apparent and the invention itself will be best understood by reference to the following description of an embodiment of the invention, when considered in conjunction with the accompanying drawings.

BEST MODE FOR CARRYING OUT THE INVENTION

Figure 1:
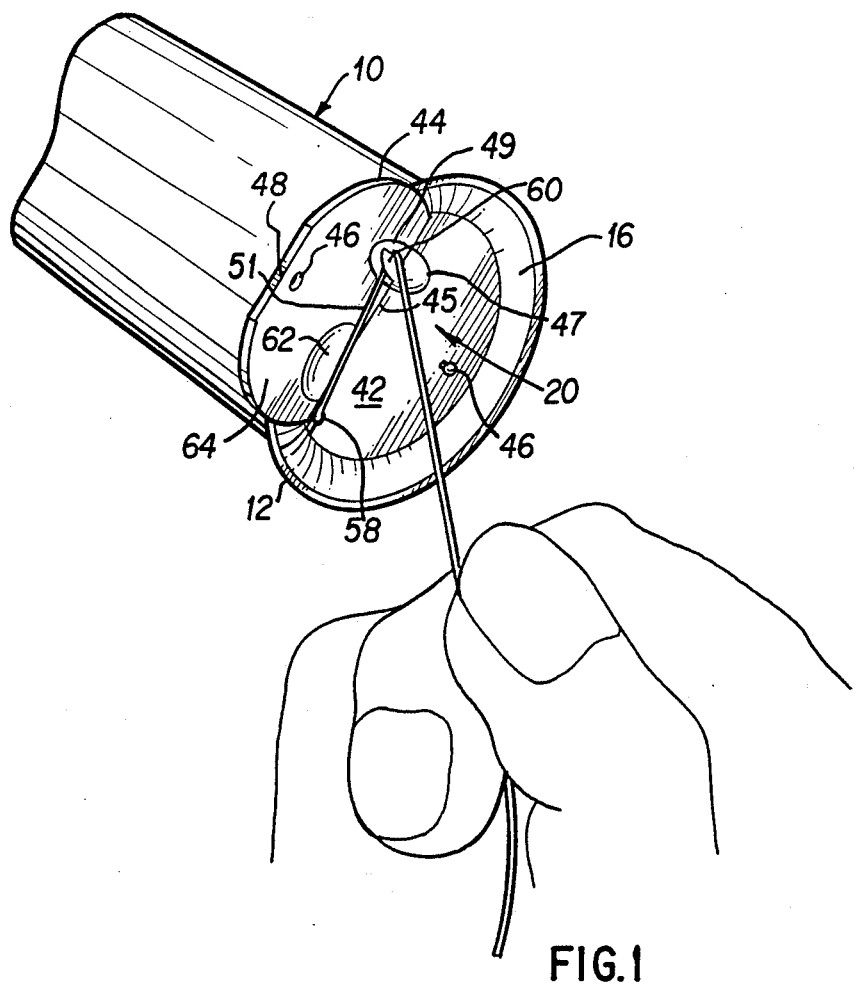
FIG. 1 is a perspective view of the end of a pump type toothpaste dispenser shown with the dental floss dispenser inserted therein, with the hinged cap raised as the user biases the dental floss against the knife blade to remove a portion of the dental floss from the spool.
Figure 2:
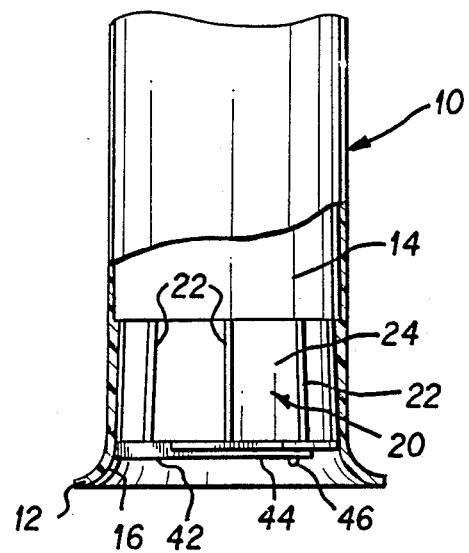
FIG. 2 is a partial sectional view of the base of the toothpaste dispenser, showing the dental floss dispenser inserted therein, with the hinged cap of the dental floss dispenser closed.

The subject matter which I regard as my invention is particularly pointed out and distinctly claimed in the claims. The structure and operation of my invention, together with further objects and advantages, may be better understood from the following description given in connection with the accompanying drawings, in which:

FIG. 1 and 2 show a toothpaste dispenser 10, having a base portion 12 adapted to receive a dental floss dispenser 20 therein. The dental floss dispenser 20 is inserted into a cavity 14 in the base of the toothpaste dispenser 10. Ribs 22 may be disposed upon the outer surface of housing 24 of the dental floss dispenser 20 to provide a light press fit of dental floss dispenser 20 into cavity 14 of toothpaste dispenser 10.

Figure 3:
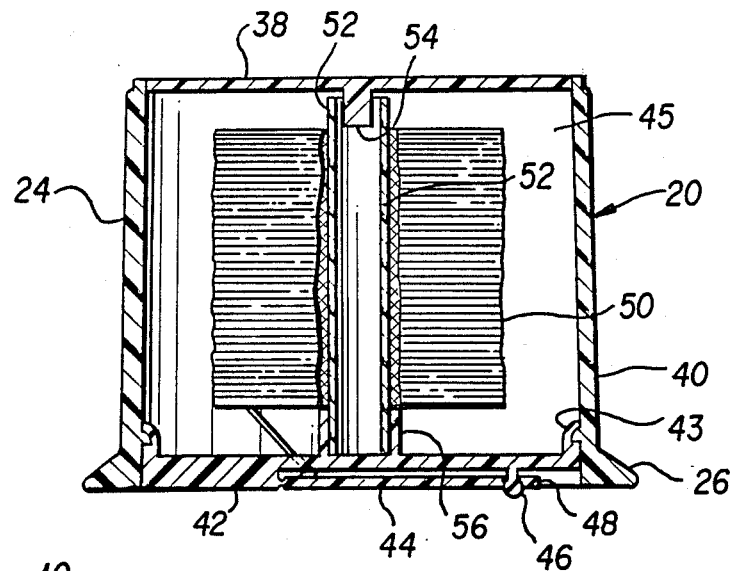
FIG. 3 is a cross sectional view of the dental floss dispenser showing the dental floss spool inserted within the dental floss dispenser housing.
Figure 5:
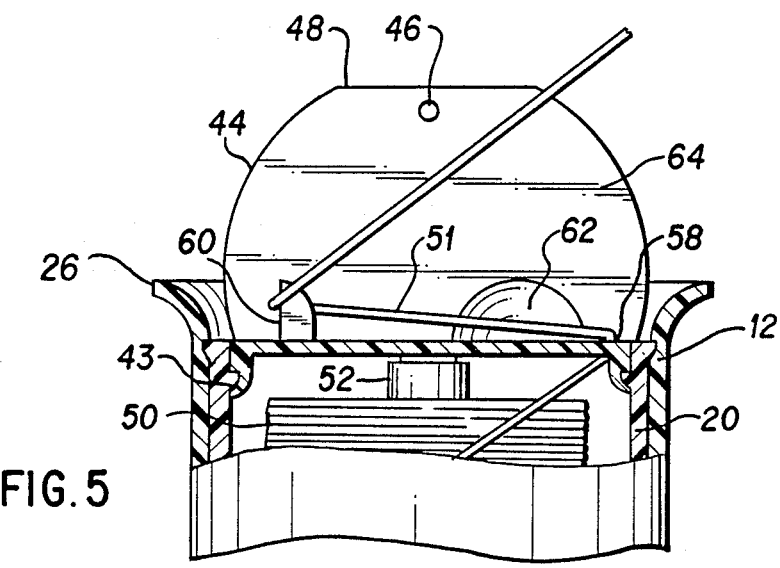
FIG. 5 is a partial cross sectional view of the dental floss dispenser showing the dental floss positioned in relation to the knife blade, in preparation for cutting a portion of the dental floss away from the remaining dental floss in the dispenser.

As best shown in FIG. 3 and FIG. 5, an annular lip 26 may extend about housing 24 to limit the depth of insertion of the dental floss dispenser 20 within cavity 14. Cavity 14 of tooth paste dispenser 10 preferably has a complimentary flaired end 16 sized to receive outer lip 26 of dental floss dispenser 20, to limit penetration of dental floss dispenser 20 within cavity 14 of tooth paste dispenser 10.

Once inserted into the base 12 of toothpaste dispenser 10, the dental floss dispenser 20 fits neatly into cavity 14, taking up no more space than required by the toothpaste dispenser 10.

As best shown in FIG. 3, the dental floss dispenser 20 comprises a housing 24 sized for insertion within cavity 14 of toothpaste dispenser 10. Housing 24 includes a base portion 38, a circumferential wall portion 40 with one end disposed adjacent to base portion 38, and a cap 42 adapted to be secured to the opposite end of circumferential wall portion 40 by any conventional manner, such as by press fit or by glueing, sonic welding, heat staking, or the like. The base portion 38, circumferential wall portion 40 and cap 42 define a chamber 45 suitable for containing dental floss therein.

Cap 42 has a hinged portion 44 which is releasably secured by conventional means, preferably with a snap closure member 46. Hinged portion 44 of cap 42 preferably has a flat portion 48 on the raised end for ease of raising hinged portion 44 away from snap closure member 46. Dental floss 50 is wound upon a spool 52 which is rotatably secured within chamber 45, preferably by a boss 54 centrally disposed to extend within chamber 45 from the base 38 of dental floss dispenser 20. Cap 42 preferably has a complementary boss 56 centrally disposed upon cap 42 to rotatably secure the opposite end of spool 52. Bosses 54, 56 may rotatably secure spool 52 internally as shown in FIG. 3 at base 38, or externally as shown in FIG. 3 at cap 42, or with any combination thereof which allows spool 52 to rotate within chamber 45. The small resistance to rotation of spool 52 is easily overcome by pulling upon the exposed end 51 of dental floss 50.

End 51 of dental floss 50 passes through an aperture 58 in cap 42 which is positioned in close proximity to hinged portion 44 of cap 42 as best shown in FIG. 1. Aperture 58 is preferably sized to closely receive the end 51 of dental floss 50 therethrough.

The exposed end 51 of dental floss 50 extends along hinged portion 44 to knife blade 60, which provides a light press fit between hinged portion 44 and knife blade 60. This serves to retain the end of dental floss between the knife blade 60 and the hinged cap 44 between use, which is not affected by the opening or closing of the hinged portion 44 of cap 42.

A flat 48 is preferably disposed upon the raised hinged portion 44 of cap 42, which provides an easy means to grasp the hinged portion to raise or lower hinged cap 44. A recess 62 is positioned between aperture 58 and knife blade 60 to allow the user's fingers to raise the end 51 of dental floss 50 away from knife blade 60. The user grasps the dental floss between their fingers, for ease of pulling a sufficient length of dental floss 50 through aperture 58 from spool 52 disposed in chamber 45 for subsequent use.

When the desired length of dental floss 50 has been withdrawn through aperture 58, the dental floss is drawn between knife blade 60 and hinged portion 44, and the dental floss is biased against knife blade 60 as shown in FIG. 1 and 5, whereupon the edge of knife blade 60 cuts dental floss 50, thereby freeing the exposed end 51 of dental floss 50 for subsequent use.

Hinged portion 44 of cap 42 is then closed and releasably secured by closure member 46. Hinged cap 44 protects the exposed portion of dental floss 50 extending between aperture 58 and knife blade 60 from accidental contamination by the outside environment during storage or transport.

The dental floss container 20 may be installed and sold as a unit with a toothpaste dispenser 10 or the dental floss dispenser 20 may be sold and used independently of the toothpaste dispenser without requiring any modification. Preferably, the dental floss dispenser 20 is sized to contain enough dental floss 50 for approximately the same number of flossings as the amount of brushings stored in the toothpaste dispenser. Whether used with a tooth paste dispenser 10 or separately, the dental floss container 20 herein disclosed, is compact, easily stored, provides a convenient dispenser for dental floss, and the hinged cap protects the dental floss from external contamination between use.

Figure 4:
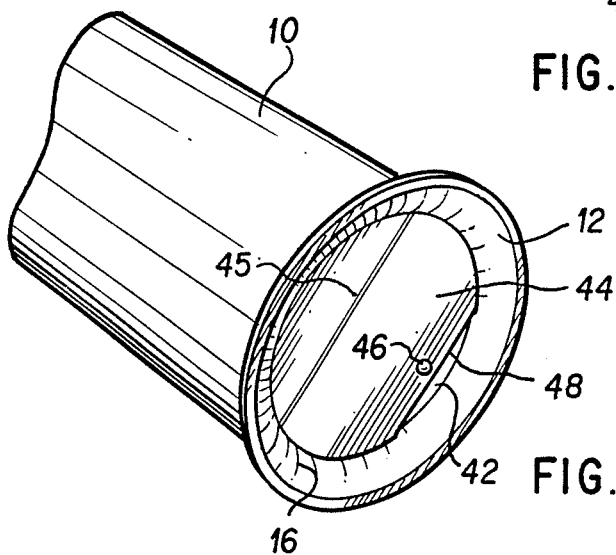
FIG. 4 is a perspective view of the end of a tooth paste dispenser shown with the dental floss dispenser inserted therein, with the protective cover closed.

In the preferred embodiment, the dental floss container 20 is inserted into cavity 14 in the base of a toothpaste dispenser 10, to provide compact storage and ready access before, during or after brushing one's teeth. Once inserted, the ribs 22 disposed upon wall portion 40 preferably serve to retain the dental floss container 20 in place within cavity 14, while an annular ring 26 disposed upon dental floss receptacle 20 limits the depth of penetration within cavity 14. For use, the toothpaste dispenser 10 is raised to expose cap 42 of dental floss receptacle 20 as shown in FIG. 4.

To expose the dental floss for subsequent use, the user raises hinged portion 44 by pressing a finger against the flat portion 48 and pulls lightly to raise the hinged portion 44 from retaining means 46 secured to cap 42. Once hinged portion 44 is raised, the user draws a finger across recess 62 to raise the end of dental floss from engagement between hinged portion 44 and knife edge 60. User grasps the end 51 of dental floss 50 and pulls to draw dental floss 50 from spool 52 through aperture 58. Once the desired length of dental floss is drawn from spool 50, the dental floss is biased against knife blade 60, to cut dental floss 50, freeing the grasped end of the dental floss for subsequent use.

Knife blade 60 retains the cut end of the dental floss 50 between knife blade 60 and hinged portion 44 of cap 42 between use.

Hinged portion 44 of cap 42 is then closed and secured to cap 42 by retaining means 46, which serves to protect the exposed portion of dental floss extending between aperture 58 and knife blade 60 from external contamination during transport or storage. Any conventional means of releasable securement may be used to secure hinged portion 44 to cap 42.

A recess 47 may be located in cap 42 to provide clearance for knife blade 60 as hinged portion 44 of cap 42 is closed between use. A recess 49 may also be provided in hinged portion 44 of cap 42 to aid in the insertion of dental floss end 51 between knife blade 60 and hinged portion 44 of cap 42, as shown in FIG. 1.

INDUSTRIAL APPLICABILITY

This invention is intended for use by consumers to aid in the storing and dispensing of dental floss. The invention may be pre-assembled within a conventional tooth paste pump dispenser, or may be sold to consumers as a separate unit. The consumer may then elect to install the invention in a tooth paste pump dispenser of their choice, or the invention may be used independently without modification by the user.

CONCLUSION

Although the invention has been illustrated and disclosed with reference to a preferred embodiment, it is to be understood that modifications may be made to the invention without departing from the spirit of the invention or from the scope of the following claims.

I claim:

1. An apparatus for dispensing dental floss, which comprises:
   (a) a housing with a base portion disposed adjacent to one end of a circumferential wall portion;
   (b) a cap secured to the opposite end of the circumferential wall portion to form a chamber between the base portion, the circumferential wall portion, and the cap;

(c) a spool rotatably secured within the chamber, the spool holding a quantity of dental floss thereon;

(d) a hinged portion releasably secured to the cap;

(e) an aperture disposed through the cap in close proximity to the hinged portion of the cap;

(f) a knife blade secured to the hinged portion in spaced relation from the aperture;

the hinged portion may be manually raised to expose an end portion of the dental floss extending through the aperture; the dental floss may be grasped and pulled to the desired length, and drawn between the hinged portion of the cap and the knife blade, and biased against the knife blade to sever the dental floss, thus capturing the end of the dental floss between the hinged portion of the cap and the knife blade, whereupon the hinged portion of the cap may be closed and releasably secured to the cap to protect an exposed portion of the dental floss from external contamination during storage or transport, and the hinged portion of the cap may be raised when desired, to expose the portion of dental floss extending between the knife blade and the aperture in preparation for subsequent use.

2. The apparatus of claim 1, wherein a recess is disposed in the hinged portion between the knife blade and the aperture, to aid in grasping the end of the dental floss.

3. The apparatus of claim 1, wherein a flat is disposed upon the hinged portion of the cap for ease of manually biasing the hinged portion of the cap.

4. The apparatus of claim 1, wherein a preferred means of releasably securing the hinged portion of the cap to the cap comprises a boss extending from the cap with a complimentary aperture sized to closely receive the boss disposed within the hinged portion of the cap, and further sized to release the hinged portion of the cap from the cap upon a light force exerted by the user upon the hinged portion of the cap.

5. The apparatus of claim 1, wherein opposing bosses extend from the base of the housing and from the cap to rotatably secure the spool within the chamber.

6. The apparatus of claim 1, wherein the aperture disposed in the cap is sized to closely receive the end of the dental floss therethrough.

7. The apparatus of claim 1, wherein the plurality of ribs are disposed about the outer surface of the circumferential wall portion of the housing, and the housing is sized to be closely received within a recess found in the base of a commercially available toothpaste dispenser.

8. The apparatus of claim 7, wherein an annular lip is disposed upon the outer circumference of the housing in proximity to the cap to limit penetration of the housing within the recess found in the base of a commercially available toothpaste dispenser.

9. The apparatus of claim 1, wherein the dental floss spool holds sufficient dental floss for approximately the same number of flossings as the number of toothpaste brushings found in a pump type toothpaste dispenser.

10. A dental floss dispenser, positioned within a cavity in the base of a pump type toothpaste dispenser, which comprises:

(a) a housing formed of a base portion and a circumferential wall portion extending from the base portion;

(b) a cap secured to one end of the circumferential wall portion to form a chamber between the base portion, the circumferential wall portion, and the cap;

(c) a spool rotatably secured within the chamber and receiving a quantity of dental floss thereon;

(d) a hinged portion extending from the cap and sized to substantially cover the cap when the hinged portion is closed;

(e) an aperture disposed through the cap in close proximity to the hinged portion of the cap;

(f) a knife blade secured to the hinged portion of the cap and disposed to expose the knife blade when the hinged portion of the cap is raised; the knife blade positioned in spaced relation from the aperture to allow the dental floss extending between the knife blade and the aperture to be grasped; wherein the hinged portion of the cap is raised to expose the dental floss extending between the knife blade and the aperture, and the dental floss is grasped to pull a length of dental floss through the aperture in the cap, whereupon the dental floss is guided between the hinged portion of the cap and the knife blade and biased to cut away a portion of the dental floss for subsequent use; and the hinged portion of the cap is lowered to close the hinged portion of the cap to protect the knife blade and a portion of dental floss extending between the knife blade and the aperture from external contamination between use.

11. The apparatus of claim 10, wherein a snap closure member is disposed between the hinged portion of the cap and the cap to releasably secure the hinged portion of the cap to the cap between use.

12. The apparatus of claim 10, wherein a plurality of ribs are disposed upon the outer circumferential wall portion of the housing to provide a light press fit between the housing and the cavity found in the base of the pump type toothpaste dispenser.

13. The apparatus of claim 10, wherein a recess is disposed in the hinged portion of the cap between the knife blade and the aperture in the cap, to aid in grasping the dental floss extending therebetween.

14. The apparatus of claim 10, wherein a flat is disposed upon the hinged portion of the cap to aid in raising and lowering the hinged portion of the cap.

15. The apparatus of claim 10 wherein opposing bosses are disposed in the base and the cap within the chamber to rotatably secure the dental floss spool therebetween.

16. An apparatus for dispensing dental floss positioned within a cavity of a pump type tooth paste dispenser, which comprises: a housing formed of a base, a circumferential wall portion extending from the base, and a cap secured to the circumferential wall portion to form a chamber therebetween;

a spool disposed within the chamber receiving dental floss thereon;

a hinged portion extending from the cap;

an aperture disposed through the cap in close proximity to the hinged portion;

a knife blade secured to the hinged portion of the cap and positioned to closely receive a strand of dental floss between the hinged portion of the cap and the knife blade;

a closure member adapted to releasably secure the hinged portion of the cap to the cap;

wherein the hinged portion of the cap is raised to expose the knife blade, aperture and a portion of the dental floss extending in spaced relation therebetween; and the dental floss is grasped and pulled to withdraw a suitable length of dental floss from the spool, and the dental floss is drawn between the knife blade and the hinged portion of the cap and biased against the knife blade to cut the dental floss, whereupon the hinged portion of the cover is lowered to releasably secure the hinged portion of the cap to the cap to protect a portion of the dental floss extending between the knife blade and the aperture from external contamination between use.

17. The apparatus of claim 16, wherein opposed bosses are disposed upon the base of the housing and the cap within the chamber to rotatably secure the dental floss spool therebetween.

18. The apparatus of claim 16, wherein a plurality of ribs are disposed upon the outer circumferential wall portion of the housing to provide a light press fit between the housing and the cavity in the pump type tooth paste dispenser.

19. The apparatus of claim 16, wherein a recess is disposed in the hinged portion of the cap between the knife blade and the aperture to aid in grasping the portion of dental floss extending between the knife blade and the aperture.

20. The apparatus of claim 16, wherein a flat is disposed upon the hinged portion of the cap to aid in raising and lowering the hinged portion during use.

* * * * *